United States Patent [19]

Hemmi et al.

[11] Patent Number: 4,963,530
[45] Date of Patent: Oct. 16, 1990

[54] RENIN INHIBITOR PEPTIDE COMPOUNDS, A PROCESS FOR THE PREPARATION THEREOF AND PHARMACEUTICAL COMPOSITION COMPRISING THE SAME

[75] Inventors: Keiji Hemmi; Masahiro Neya; Keisuke Imai; Natsuko Kayakiri; Masashi Hashimoto, all of Tsukuba, Japan

[73] Assignee: Fujisawa Pharmaceutical Company, Ltd., Osaka, Japan

[21] Appl. No.: 171,269

[22] Filed: Mar. 21, 1988

[30] Foreign Application Priority Data

Mar. 27, 1987 [GB] United Kingdom ............... 8707412

[51] Int. Cl.$^5$ .................. H61K 37/02; C07K 5/06
[52] U.S. Cl. ........................... 514/19; 544/58.4; 544/139; 544/370; 546/146; 546/165; 546/210; 546/278; 548/336; 548/344
[58] Field of Search ............ 514/19; 544/58.4, 139, 544/370; 546/146, 165, 210, 278; 548/336, 344

[56] References Cited

U.S. PATENT DOCUMENTS

| | | | |
|---|---|---|---|
| 4,073,905 | 2/1978 | Kummer et al. | 544/139 |
| 4,656,269 | 4/1987 | Iizuka et al. | 544/139 |
| 4,698,329 | 10/1987 | Matsueda et al. | 548/200 |
| 4,711,958 | 12/1987 | Iizuka et al. | 544/139 |

FOREIGN PATENT DOCUMENTS

| | | |
|---|---|---|
| 152255 | 2/1985 | European Pat. Off. |
| 172346 | 2/1986 | European Pat. Off. |
| 200406 | 12/1986 | European Pat. Off. |
| 206807 | 12/1986 | European Pat. Off. |
| 229667 | 1/1987 | European Pat. Off. |
| 231919 | 2/1987 | European Pat. Off. |
| 264795 | 10/1987 | European Pat. Off. |

Primary Examiner—Lester L. Lee
Attorney, Agent, or Firm—Oblon, Spivak, McClelland, Maier & Neustadt

[57] ABSTRACT

A compound of the formula:

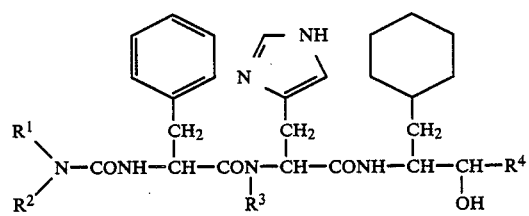

wherein
  $R^1$ is aryl optionally substituted with a substituent selected from the group consisting of halogen and halo(lower)alkyl; lower alkyl or cyclo(lower)alkyl; and
  $R^2$ is hydrogen or lower alkyl, or
  $R^1$ and $R^2$ are taken together with the attached nitrogen atom to form a heterocyclic group optionally substituted with a substituent selected from the group consisting of lower alkyl and esterified carboxy,
  $R^3$ is hydrogen or lower alkyl, and
  $R^4$ is lower alkyl, and its pharmaceutically acceptable salt, a process for the preparation thereof and pharmaceutical composition comprising the same.

10 Claims, No Drawings

RENIN INHIBITOR PEPTIDE COMPOUNDS, A PROCESS FOR THE PREPARATION THEREOF AND PHARMACEUTICAL COMPOSITION COMPRISING THE SAME

This invention relates to new peptide compounds and pharmaceutically acceptable salts thereof.

More particularly, it relates to new peptide compounds and pharmaceutically acceptable salts thereof which have inhibitory activities against renin, to a process for the preparation thereof, to a pharmaceutical composition comprising the same and to a method for the treatment of hypertension in human being or animals.

One object of this invention is to provide new and useful peptide compounds and pharmaceutically acceptable salts thereof which possess inhibitory activities against renin, and which are useful as a hypotensor, especially for oral administration.

Another object of this invention is to provide a process for the preparation of said peptide compounds and salts thereof.

A further object of this invention is to provide a pharmaceutical composition comprising, as an active ingredient, said peptide compounds and pharmaceutically acceptable salts thereof.

Still further object of this invention is to provide a therapeutical method for the treatment of hypertension.

The object peptide compounds of this invention are new and can be represented by the following general formula [I]:

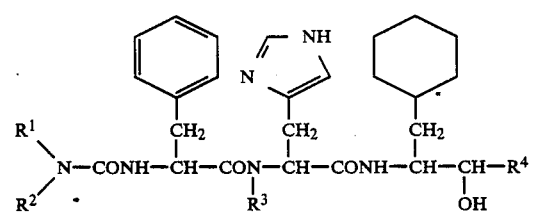

[I]

wherein
  $R^1$ is aryl optionally substituted with a substituent selected from the group consisting of halogen and halo(lower)alkyl; lower alkyl or cyclo(lower)alkyl; and
  $R^2$ is hydrogen or lower alkyl, or
  $R^1$ and $R^2$ are taken together with the attached nitrogen atom to form a heterocyclic group optionally substituted with a substituent selected from the group consisting of lower alkyl and esterified carboxy,
  $R^3$ is hydrogen or lower alkyl, and
  $R^4$ is lower alkyl.

The object compound [I] or its salt can be prepared by a process as illustrated in the following reaction schemes, but preparations of the object compound [I] are not limited to the following process.

Process 1

Step 1

-continued

Process 1

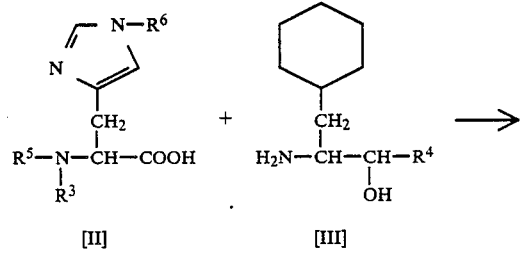

[II]

or its reactive derivative at the carboxy group or a salt thereof

[III]

or its reactive derivative at the amino group or a salt thereof

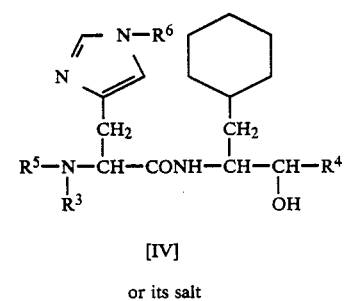

[IV]

or its salt

Step 2

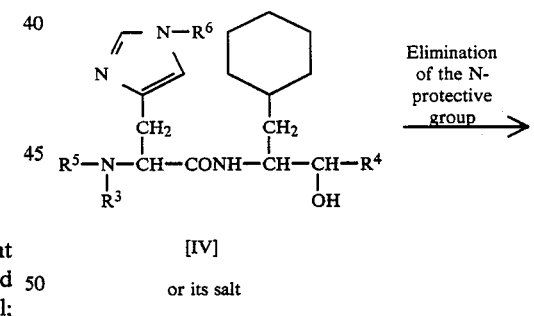

[IV]

or its salt

Elimination of the N-protective group

Step 3

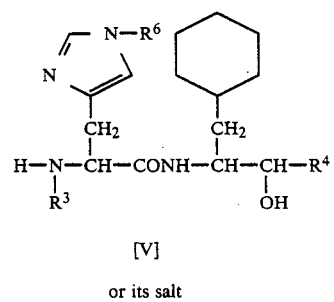

[V]

or its salt

-continued
Process 1

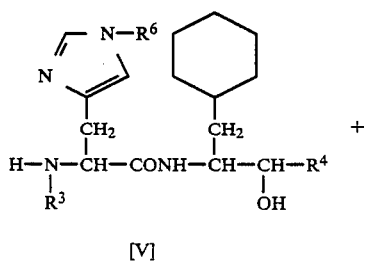

[V]

or its reactive
derivative at the
amino group or a
salt thereof

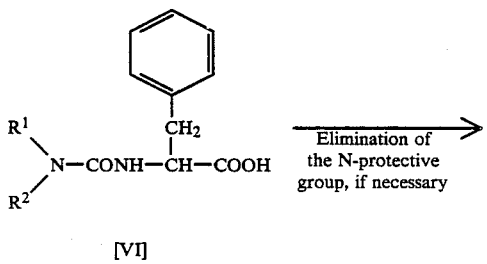

[VI]

or its reactive derivative
at the carboxy group or a
salt thereof

Elimination of
the N-protective
group, if necessary ⟶

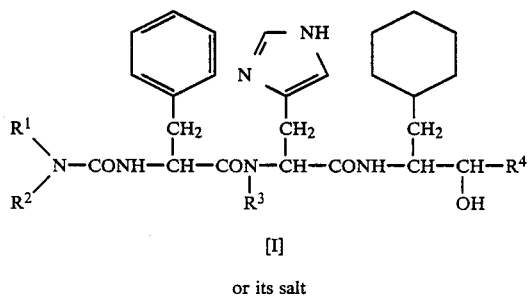

[I]

or its salt wherein
$R^5$ is an N-protective group,
$R^6$ is hydrogen or an N-protective group, and
$R^1$, $R^2$, $R^3$ and $R^4$ are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "aryl" moiety in the term "aryl optionally substituted with a substituent selected from the group consisting of halogen and halo(lower)alkyl" may be phenyl, naphthyl, tolyl, xylyl, mesityl, cumenyl, and the like, in which preferable one is phenyl, and the aryl moiety thus explained is optionally substituted with a substituent selected from the group consisting of halogen [e.g. fluoro, chloro, bromo and iodo] and halo(lower)alkyl, preferably mono-, di- or tri(halo)-lower alkyl [e.g. chloromethyl, bromomethyl, fluoromethyl, dichloromethyl, difluoromethyl, trifluoromethyl, 2-chloroethyl, 2-bromoethyl, 3-chloropropyl, etc.].

Preferable example of "aryl optionally substituted with a substituent selected from the group consisting of halogen and halo(lower)alkyl" thus defined may be phenyl, halophenyl [e.g. fluorophenyl, chlorophenyl, bromophenyl, iodophenyl, etc.], and mono-, di- or tri(-halo)lower alkylphenyl [e.g. chloromethylphenyl, dichloromethylphenyl, trifluoromethylphenyl, etc.], in which most preferable ones are fluorophenyl and trifluoromethylphenyl.

Suitable "lower alkyl" may be a straight or branched one such as methyl, ethyl, propyl, isopropyl, butyl, isobutyl, tert-butyl, pentyl, isopentyl, hexyl, and the like, in which more preferable one may be $C_1$–$C_5$ alkyl.

Suitable "cyclo(lower)alkyl" may be cyclopropyl, cyclobutyl, cyclopentyl, cyclohexyl, and the like in which most preferable one is cyclohexyl.

Suitable "heterocyclic group" formed by $R^1$, $R^2$ and the attached nitrogen atom may be morpholino, thiomorpholino, pyrrolidin-1-yl, piperidino, piperazin-1-yl, pyrrolin-1-yl, 1,4-dihydropyridin-1-yl, 1,2,3,6-tetrahydropyridin-1-yl, 1,2,3,4-tetrahydroisoquinolin-2-yl, 1,2,3,4-tetrahydroquinolin-1-yl, or the like, in which the most preferable ones are morpholino, thiomorpholino, piperazin-1-yl, pyrrolidin-1-yl and 1,2,3,4-tetrahydroisoquinolin-2-yl, and the heterocyclic group thus explained is optionally substituted with a substituent selected from the group consisting of the above-mentioned lower alkyl and esterified carboxy, preferably lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], in which the most preferable ones are 4-methylpiperazin-1-yl and 2-methoxycarbonylpyrrolidin-1-yl.

Suitable "N-protective group" may be acyl such as substituted or unsubstituted lower alkanoyl [e.g. formyl, acetyl, propionyl, trifluoroacetyl, etc.], phthaloyl, lower alkoxycarbonyl [e.g. tertbutoxycarbonyl, tert-amyloxycarbonyl, etc.], substituted or unsubstituted aralkyloxycarbonyl [e.g. benzyloxycarbonyl, p-nitrobenzyloxycarbonyl, etc.], substituted or unsubstituted arenesulfonyl [e.g. benzenesulfonyl, tosyl, etc.], nitrophenylsulfenyl, or the like, aralkyl [e.g. trityl, benzyl, etc.] or the like.

Suitable pharmaceutically acceptable salts of the object compounds [I] are conventional non-toxic salts and include an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. aspartic acid salt, glutamic acid salt, etc.], or the like.

The process for preparing the object compound [I] are explained in detail in the following.

Process 1

Step 1

The compound [IV] or its salt can be prepared by reacting a compound [II] or its reactive derivative at the carboxy group or a salt thereof with a compound [III] or its reactive derivative at the amino group or a salt thereof.

Suitable salts of the compound [IV] can be referred to the ones as exemplified for the compound [I].

Suitable reactive derivative at the carboxy group of the compound [II] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenyphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-diemthylhydroxylamine, 1,-hydroxy-2-)1H)-pyridone, N-hydroxysuccinimide, N-hydroxyphthalimide, 1-hydroxy-1H-benzotriazole, etc.], and the like. These reactive derivatives can optionally be selected from them according to the kind of the compound [II] to be used.

Suitable salts of the compound [II] and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N, N'-dibenzylethylenediamine salt, etc.], or the like and an acid addition salt as exemplified for the compound [I].

Suitable reactive derivative at the amino group of the compound [III] may include Schiff's base type imino or its tautomeric enamine type isomer formed by the reaction of the compound [III] with a carbonyl compound such as aldehyde, ketone or the like; a silyl derivative formed by the reaction of the compound [III] with a silyl compound such as bis(trimethylsilyl)acetamide, mono(trimethylsilyl)acetamide, bis(trimethylsilyl)urea or the like; a derivative formed by reaction of the compound [III] with phosphorus trichloride or phosgene, and the like.

Suitable salts of the compound [III] and its reactive derivative can be referred to the ones as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-diemthylformamide, pyridien or any other organic solvent which does not adversely influence the reaction. These conventional solvent may also be used in a mixture with water.

In this reaction, when the compound [II] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isipropyl chloroformate, etc.]; triphenylphosphine; 2-ethyl-7- hydroxybenzisoxazolium salt; 2-ethyl-5-(m-sulfophenyl)-isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Step 2

The compound [V] or its salt can be prepared by subjecting a compound [IV] or its salt to elimination reaction of the N-protective group.

Suitable salts of the compound [V] can be referred to the ones as exemplified for the compound [I].

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the abovementioned acids to be used in chemical reduction are in liquid, they can also be used as a solvent. Further, a suitable solvent to be used in catalytic reduction may be the abovementioned solvent, and other conventional solvent such as diethyl ether, dioxane, tetrahydrofuran, etc., or a mixture thereof.

The reaction temperature of this reduction is not critical and the reaction is usually carried out under cooling to heating.

Step 3

The object compound [I] or its salt can be prepared by reacting a compound [V] or its reactive derivative at the amino group or a salt thereof with a compound [VI] or its reactive derivative at the carboxy group or a salt thereof, and if necessary, eliminating the N-protective group.

Suitable salts of the compound [VI] can be referred to a base salt as exemplified for the compound [II].

This reaction can be carried out in substantially the same manner as Step 1, and therefore the reaction made and reaction conditions [e.g. reactive derivatives, condensing agents, solvents, reaction temperature, etc.] of this reaction are to be referred to those as explained in Step 1.

In case that the imidazolyl group of the compound [V] is protected, the object compound [I] can be prepared by further eliminating the N-protective group of the reaction product of the compound [V] with the compound [VI].

This elimination reaction can be carried out in substantially the same manner as Step 2 in this process, and therefore the reaction mode and reaction conditions [e.g. bases, acids, reducing agents, catalysts, solvents, reaction temperature, etc.] of this reaction are to be referred to those as explained in Step 2 in this process.

Among the starting compound, some of them are new and can be prepared by processes as illustrated in the following reaction schemes.

Process A

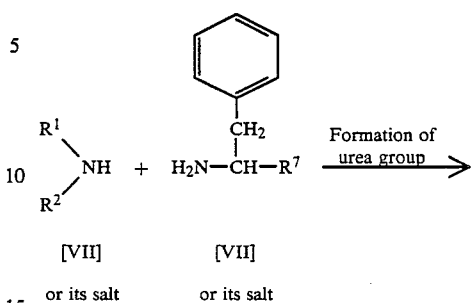

Process B

Process C

-continued

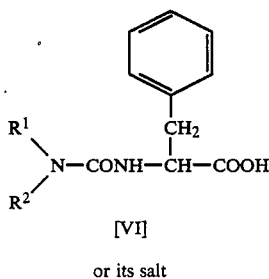

[VI]

or its salt wherein
R[7] is protected carboxy, and
R[1] and R[2] are each as defined above.

Suitable "protected carboxy" may be carboxy group protected by conventional protective group such as lower alkoxy-carbonyl [e.g. methoxy-carbonyl, ethoxy-carbonyl, propoxy-carbonyl, isopropoxy-carbonyl, botoxy-carbonyl, sec-butoxy-carbonyl, isobutoxy-carbonyl, tert-butoxy-carbonyl, pentyloxy-carbonyl, neopentyloxy-carbonyl, hexyloxy-carbonyl, etc.], optionally substituted ar(lower)alkoxy-carbonyl for example, mono or di or triphenyl(lower)alkoxy-carbonyl which may be substituted with nitro [e.g. benzyloxy-carbonyl, 4-nitrobenzyloxycarbonyl, benzhydryloxy-carbonyl, trityloxy-carbonyl, etc.], of the like.

The above-mentioned processes for preparing the starting compounds are explained in detail in the following.

Process A

The compound [IX] can be prepared by subjecting a compound [VII] or its salt and a compound [VIII] or its salt to formation reaction of urea group.

Suitable salts of the compounds [VII] and [VIII] can be referred to the ones as exemplified for the compound [I]

This reaction is carried out in the presence of reagent which introduces carbonyl group such as phosgene, haloformate compound [e.g. ethyl chloroformate, trichloromethyl chloroformate etc.], N,N'-carbonyldiimidazole, metal carbonyl compounds [e.g. cobalt carbonyl, manganese carbonyl, etc.], a combination of carbon monoxide and catalysts such as palladium chloride, etc., or the like.

This reaction is usually carried out in a solvent such as dioxane, tetrahydrofuran, benzene, toluene, chloroform, methylene chloride, N,N-dimethylformamide or any other organic solvent which does not adversely influence the reaction.

The reaction temperature is not critical and the reaction is usually carried out under cooling to heating.

Process B

The compound [IXa] can be prepared by reacting a compound [X] with a compound [VIII] or its salt.

This reaction is usually carried out in a solvent such as dioxane, tetrahydrofuran, benzene, chloroform, methylene chloride, N,N-dimethylformamide or any other organic solvent which does not adversely influence the reaction.

The reaction temperature is not critical and the reaction is usually carried out under cooling to heating.

Process C

The compound [VI] or its salt can be prepared by subjecting a compound [IX] to elimination reaction of the carboxy-protective group.

This reaction can be carried out in substantially the same manner as Step 2 in Process 1, and therefore the reaction mode and reaction conditions [e.g. bases, acids, reducing agents, catalysts, solvents, reaction temperature, etc.] of this reaction are to be referred to those as explained in Step 2 in Process 1.

The compounds obtained by the above processes can be isolated and purified by a conventional method such as pulverization, recrystallization, column chromatography, reprecipitation, or the like.

It is to be noted that the compound [I] and the other compounds may include one or more stereoisomers due to asymmetric carbon atoms, and all of such isomers and mixture thereof are included within the scope of this invention.

The object compounds [I] and pharmaceutically acceptable salts thereof possess strong inhibitory activities against renin, and useful as a hypotensor, especially for oral administration.

For therapeutic purpose, the compounds [I] and pharmaceutically acceptable salts thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compounds [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating hypertension. In general, amounts between 0.1 mg/body and about 1,000 mg/body may be administered per day.

In order to illustrate the usefulness of the object compound [I], the pharmacological test data of some representative compounds of the compound [I] are shown in the following.

Test Compounds (a) 2(S)-(N-Morpholinocarbonyl-L-phenylalanyl-L-histidyl)amino-1-cyclohexyl-3(S)-hydroxy-6-methylheptane (b) 2(S)-(N-Morpholinocarbonyl-L-phenylalanyl-N$^\alpha$-methyl-L-histidyl)amino-1-cyclohexyl-3(S)-hydroxy-6-methylheptane (c) 2(S)-(N-Thiomorpholinocarbonyl-L-phenylalanyl-N$^\alpha$-methyl-L-histidyl)amino-1-cyclohexyl-3(S)-hydroxy-6-methylheptane (d) 2(S)-[N-(1,2,3,4-Tetrahydroisoquinolin-2-ylcarbonyl)-L-phenylalanyl-N$^\alpha$-methyl-L-histidyl]amino-1-cyclohexyl-3(S)-hydroxy-6-methylheptane Test 1

Test Method

Human plasma was collected from male volunteers pretreated with no drugs and used as a pool. Disodium salt of ethylenediaminetetraacetic acid (EDTA) was used as the anticoagulant. Plasma renin activity was measured as the rate of angiotensin I (Ang I) formation after incubation (37° C.) of the endogenous renin and angiotensinogen in plasma at pH 6.0. The incubation mixture contained 250 μl of plasma, 5 μl of (phenylmethyl)sulfonyl fluoride, 30 μl of buffer (sodium, potassium-phosphate, pH 6.0), and 15 μl of an appropriate concentration of test compound in 50% ethyl alcohol-water vehicle. The Ang I formed after 90 minutes of incubation was measured by radioimmunoassay (RIA) which was carried out with a commercial kit, RENCTK 100 (manufactured by Commissariat A L'energie Atomique). Samples were incubated in duplicate and each tube was measured in duplicate in the RIA. Percentage inhibition of plasma renin activity was calculated by comparing the amount of Ang I produced with and without a test compound. The concentration of test compound that inhibited plasma renin activity by 50% ) ($IC_{50}$) was determined by Probit method.

| Test Results | |
|---|---|
| Test Compound | $IC_{50}$ (M) |
| (a) | $6.1 \times 10^{-8}$ |
| (b) | $2.1 \times 10^{-8}$ |
| (c) | $2.4 \times 10^{-8}$ |
| (d) | $6.0 \times 10^{-8}$ |

Test 2
Test Method

Male or female cynomolgus monkeys (*Macaca fascicularis*) weighing about 2.5–3.5 kg were used. Sodium depletion was achieved by administering furosemide, 15 mg/kg subcutaneously one day before and then 10 mg/kg intravenously 30 minutes before the administration of the test compound.

Test compounds were dissolved in diluted equimolar hydrochloric acid (pH 5–6) and orally administered to conscious and trained monkeys placed in restraining chairs with pneumatic cuff positioned around the arm for oscillometric measurement of mean arterial blood pressure (MAP) (Model BP-203 NPJ, manufactured by Nippon Colin).

The MAP was measured at 0 (predosing base line), 0.5, 1, 2, 3, 4 and 6 hours after administration of the test compound. The maximum hypotensive effect was calculated as the maximum percentage fall of MAP from the pretreatment value.

Blood samples were collected at 0, 0.5, 1, 2, 4 and 6 hours after dosing from the antecubital vein of the monkey into disodium salt of EDTA coated tubes, centrifuged for 10 min (3000 rpm, 4° C.) and plasmas were obtained for determination of plasma renin activity (PRA). PRA was measured as the rate of Ang I formation with the same principle as illustrated in Test 1. 100 μl of sample plasma was mixed with 100 μl of the solution of angiotensinase inhibitors (3 mM 8-hydroxyquinoline sulfate and 5 mM 2,3-dimercaptopropanol, SB-REN-1, SORIN BIOMEDICA, Italy). Half (100 μl) of the mixture was incubated at 37° C. for one hour and Ang I formed was determined by a commercial RIA kit (DINABOTT). The remaining half (100 μl) of the reaction mixture was kept at 4° C. for one hour to measure and correct for the preexisting Ang I in the plasma. Percentage inhibition of PRA was calculated by the following formula:

$$\text{Inhibition (\%)} = \left(1 - \frac{D_{37} - D_4}{A_{37} - A_4}\right) \times 100$$

$A_{37}$: the amount of angiotensin I formed by incubation at 37° C. of plasma collected before dosing the test compound $A_4$: the amount of angiotensin I formed by keeping at 4° C. of plasma collected before dosing the test compound $D_{37}$: the amount of angiotensin I formed by incubation at 37° C. of plasma collected after dosing the test compound $D_4$: the amount of angiotensin I formed by keeping at 4° C. of plasma collected after dosing the test compound.

| Test Results | | |
|---|---|---|
| Test Compound | Dose [mg/kg(po)] | Maximum hypotensive effect (%) | Maximum inhibition of PRA (%) |
| (b) | 32 | 25 | 96 |

The following Examples are given for the purpose of illustrating preferable preparations of the object compounds [I], and preparations of said compounds are not limited to the following Examples.

In the following Examples, Kieselgel 60F 254 (Trademark: manufactured by Merck & Co.) (thickness: 0.25 mm) was used as TLC plate.

EXAMPLE 1

(1) To a solution of N-t-butoxycarbonyl-L-cyclohexylalaninal (7.73 g) in dry tetrahydrofuran (200 ml) which was cooled to −78° C., was added dropwise a solution of isopentyl magnesium bromide prepared from isopentyl bromide (46.4 g) and magnesium (7.47 g) in dry tetrahydrofuran (500 ml). After the addition was completed, the reaction mixture was allowed to warm to ambient temperature for 2 hours and was poured into saturated aqueous ammonium chloride (500 ml). The resulting mixture was extracted with ether (500 ml×2), and the extract was combined, dried over magnesium sulfate and evaporated to give an oil (10.1 g). The residue was purified with silica gel (1 kg) column chromatography (10% ethyl acetate in hexane as eluent), to give 2(S)-t-butoxycarbonylamino-1-cyclohexyl-3(S)-hydroxy-6-methylheptane (3.03 g).

Rf: 0.67 (benzene: ethyl acetate, 4:1, V/V).

$[\alpha]_D^{20}$: −23.46° (c 1.0, MeOH).

(2) A solution of 2(S)-t-butoxycarbonylamino-1-cyclohexyl-3(S)-hydroxy-6-methylheptane (600 mg) in trifluoroacetic acid (10 ml) was stirred at 0° C. for 30 minutes. After evaporation of the solvent, the residue was dissolved in ethyl acetate (20 ml). The solution was washed with saturated sodium bicarbonate solution, dried over magnesium sulfate, and evaporated in vacuo to give 2(S)-amino-1-cyclohexyl-3(S)-hydroxy-6-methylheptane (412 mg) as an oil.

Rf: 0.63 (chloroform: methanol: acetic acid, 8:1:1, V/V).

(3) To a solution of $N^\alpha$-t-butoxycarbonyl-$N^\alpha$-methyl-$N^{im}$-tosyl-L-histidine (2.77 g) and 2(S)-amino-1-cyclohexyl-3(S)-hydroxy-6-methylheptane (1.49 g) in dry methylene chloride (60 ml) which was cooled at 0° C., was added N-ethyl-N'-(3-dimethylaminopropyl)carbodiimide (1.25 g). The mixture was stirred at ambient temperature for 3 hours. After evaporation of the solvent, the residue was dissolved in ethyl acetate (200 ml) and the solution was washed with 0.5% hydrochloric acid, saturated sodium bicarbonate solution and water successively, dried over magnesium sulfate, and concentrated under reduced pressure. The residue was purified with silica gel column chromatography (1% methanol in chloroform as eluent) to give 2(S)-(N$^\alpha$-t-butoxycarbonyl-N$^\alpha$-methyl-N$^{im}$-tosyl-L-histidyl)amino-1-cyclohexyl-3(S)-hydroxy-6-methylheptane (1.61 g) as an amorphous powder.

mp: 55°–58° C.

Rf: 0.56 (benzene: ethyl acetate: acetic acid, 20:20:1 V/V).

(4) A solution of 2(S)-(N$^\alpha$-t-butoxycarbonyl-N$^\alpha$-methyl-N$^{im}$-tosyl-L-histidyl)amino-1-cyclohexyl-3(S)-hydroxy-6-methylheptane (1.20 g) in trifluoroacetic acid (20 ml) was stirred at −5° C. for 3 hours. After concentration of the mixture in vacuo, the residue was dissolved in ethyl acetate (100 ml). The solution was washed with saturated sodium bicarbonate solution, dried over magnesium sulfate, and concentrated in vacuo to give 2(S)-(N$^\alpha$-methyl-N$^{im}$-tosyl-L-histidyl)amino-1-cyclohexyl-3(S)-hydroxy-6-methylheptane (982 mg) as an oil.

Rf: 0.67 (chloroform: methanol, 10:1, V/V).

(5) To a solution of L-phenylalanine benzyl ester p-toluenesulfonic acid salt (4.27 g) in dry toluene (50 ml) was added triethylamine (1.01 g) and trichloromethyl chloroformate (0.732 ml). The mixture was stirred at 80° C. for 30 minutes. After evaporation of the solvent, the residue was dissolved in dry tetrahydrofuran (40 ml) and morpholine (871 mg) was added to the solution at ambient temperature. The mixture was stirred at the same temperature for 3 hours. After evaporation of the solvent, the residue was dissolved in ethyl acetate (100 ml) and the solution was washed with 5% hydrochloric acid, saturated sodium bicarbonate solution and water successively, dried over magnesium sulfate, and concentrated under reduced pressure. The residue was purified with silica gel column chromatography (30% ethyl acetate in n-hexane as eluent) to give N-morpholinocarbonyl-L-phenylalanine benzyl ester (3.02 g) as an amorphous powder.

mp: 85°–87° C.

Rf: 0.30 (ethyl acetate: n-hexane, 1:1,V/V).

(6) A solution of N-morpholinocarbonyl-L-phenylalanine benzyl ester (1.43 g) in methanol (20 ml) was hydrogenated over 10% palladium on carbon (150 mg) at 3 atmospheric pressure of hydrogen for 1 hour. The solution was filtered and concentrated in vacuo to give N-morpholinocarbonyl-L-phenylalanine (1.02 g) as an amorphous powder.

mp: 57°–60° C.

Rf: 0.15 (chloroform: methanol, 10:1,V/V).

(7) To a solution of N-morpholinocarbonyl-L-phenylalanine (663 mg) and 2(S)-(N$^\alpha$-methyl-N$^{im}$-tosyl-Lhistidyl)amino-1-cyclohexyl-3(S)-hydroxy-6-methylheptane (982 mg) in dry methylene chloride (30 ml), which was cooled to 0° C., was added N-ethyl-N'-(3-dimethylaminopropyl)carbodiimide hydrochloride (437 mg). The mixture was stirred at the same temperature for 6 hours. After evaporation of the solvent, the residue was dissolved in ethyl acetate (60 ml) and the solution was washed with 5% hydrochloric acid, saturated sodium bicarbonate solution, and water, successively, dried over sodium sulfate, and concentrated under reduced pressure. After the residue was dissolved in N,N-dimethylformamide (30 ml), pyridine hydrochloride (2.20 g) was added to the solution at ambient temperature. The mixture was stirred at the same temperature for 2 hours. After evaporation of the solvent, the residue was dissolved in ethyl acetate (100 ml) and the solution was washed with water, saturated sodium bicarbonate solution and water successively, dried over magnesium sulfate, and concentrated under reduced pressure. The residue was purified with silica gel column chromatography (2% methanol in chloroform as eluent) to give 2(S)-(N-morpholinocarbonyl-L-phenylalanyl-N$^\alpha$-methyl-L-histidyl)amino-1-cyclohexyl-3(S)-hydroxy-6-methylheptane (1.03 g) as an amorphous powder.

mp: 102°–108° C.

Rf: 0.58 (chloroform : methanol, 10:1, V/V).

EXAMPLE 2

(1) To a solution of N-t-butoxycarbonyl-L-histidine (363 mg) and 2(S)-amino-1-cyclohexyl-3(S)-hydroxy-6-methylheptane (294 mg) in dry N,N-dimethylformamide (30 ml) which was cooled to 0° C., were added a solution of diphenyl phosphorylazide (390 mg) in dry N,N-dimethylformamide (5 ml) and triethylamine (144 mg). The mixture was stirred overnight at ambient temperature. After evaporation of the solvent, the residue was dissolved in ethyl acetate (30 ml) and the solution was washed with 10% citric acid solution, saturated sodium bicarbonate solution and water successively, dried over magnesium sulfate, and concentrated under reduced pressure. The residue was purified with silica gel column chromatography (chloroform as eluent) to give 2(S)-(N-t-butoxycarbonyl-L-histidyl)amino-1-cyclohexyl-3(S)-hydroxy-6-methylheptane (384 mg) as an amorphous powder.

mp: 96°–100° C.

Rf: 0.47 (chloroform: methanol: acetic acid, 8:1:1, V/V).

(2) A solution of 2(S)-(N-t-butoxycarbonyl-L-histidyl)amino-1-cyclohexyl-3(S)-hydroxy-6-methylheptane (383 mg) in trifluoroacetic acid (10 ml) was stirred at 0° C. for 30 minutes. After concentration of the mixture in vacuo, the residue was dissolved in ethyl acetate (20 ml). The solution was washed with saturated sodium bicarbonate solution, dried over magnesium sulfate, and concentrated in vacuo to give 2(S)-(L-histidyl)amino-1-cyclohexyl-3(S)-hydroxy-6-methylheptane (275 mg) as an amorphous powder.

mp: 126°–130° C.

Rf: 0.11 (chloroform: methanol: acetic acid, 8:1:1, V/V).

(3) To a solution of N-morpholinocarbonyl-L-phenylalanine (114 mg) and 2(S)-(L-histidyl)amino-1-cyclohexyl-3(S)-hydroxy-6-methylheptane (150 mg) in dry N,N-dimethylformamide (20 ml) which was cooled to 0° C., were added a solution of diphenyl phosphorylazide (125 mg) in dry N,N-dimethylformamide (5 ml) and triethylamine (46 mg). The mixture was stirred overnight at ambient temperature. After evaporation of the solvent, the residue was dissolved in ethyl acetate (30 ml) and the solution was washed with saturated sodium bicarbonate solution and water successively, dried over magnesium sulfate, and concentrated under reduced pressure. The residue was purified with silica gel column chromatography (2% methanol in chloroform as eluent) to give 2(S)-(N-morpholinocarbonyl-L-phenylalanyl-L-histidyl)amino-1-cyclohexyl-3(S)-hydroxy-6-methylheptane (174 mg) as an amorphous powder.

mp: 108°–110° C.

Rf: 0.41 (chloroform: methanol, 6:1,V/V).

EXAMPLE 3

(1) N Thiomorpholinocarbonyl-L-phenylalanine benzyl ester (576 mg) was obtained according to a similar manner to that of Example 1-(5) from L-phenylalanine benzyl ester p-toluenesulfonic acid salt (1.71 g) and thiomorpholine (454 mg).

mp: 101°–103° C.

Rf: 0.70 (n-hexane: ethyl acetate, 1:1,V/V).

(2) To a solution of N-thiomorpholinocarbonyl-L-phenylalanine benzyl ester (526 mg) in a mixture of methanol (10 ml) and water (10 ml) which was cooled to 0° C., was added 1N sodium hydroxide solution (4 ml). The mixture was stirred at the same temperature for 1 hour. After evaporation of methanol, remaining aqueous solution was washed with diethyl ether, acidified to pH 2.5 with 3N hydrochloric acid and extracted with ethyl acetate (30 ml×3). The extract was washed with saturated sodium chloride solution, dried over magnesium sulfate and concentrated under reduced pressure to give N-thiomorpholinocarbonyl-L-phenylalanine (382 mg) as an oil.

Rf: 0.10 (chloroform: methanol, 9:1,V/V).

(3) 2(S)-(N-Thiomorpholinocarbonyl-L-phenylalanyl-N$^\alpha$-methyl-L-histidyl)amino-1-cyclohexyl-3(S)-hydroxy-6-methylheptane (80.7 mg) was obtained according to a similar manner to that of Example 1-(7) from N-thiomorpholinocarbonyl-L-phenylalanine (55 mg) and 2(S)-(N$^\alpha$-methyl-N$^{im}$-tosyl-L-histidyl)amino-1-cyclohexyl-3(S)-hydroxy-6-methylheptane (90 mg).

mp: 106°–110° C.

Rf: 0.53 (chloroform: methanol, 9:1,V/V).

EXAMPLE 4

(1) N-(1,2,3,4-Tetrahydroisoquinolin-2-ylcarbonyl)-L-phenylalanine benzyl ester (1.02 g) was obtained according to a similar manner to that of Example 1-(5) from L-phenylalanine benzyl ester p-toluenesulfonic acid salt (1.71 g) and 1,2,3,4-tetrahydroisoquinoline (586 mg).

Rf: 0.61 (n-hexane: ethyl acetate, 1:2, V/V).

(2) N-(1,2,3,4-Tetrahydroisoquinolin-2-ylcarbonyl)-L-phenylalanine (730 mg) was obtained according to a similar manner to that of Example 1-(6) from N-(1,2,3,4-tetrahydroisoquinolin-2-ylcarbonyl)-L-phenylalanine benzyl ester (950 mg).

Rf: 0.19 (chloroform: methanol, 10:1, V/V).

(3) 2(S)-[N-(1,2,3,4-Tetrahydroisoquinolin-2-ylcarbonyl)-L-phenylalanyl-N$^\alpha$-methyl-L-histidyl]amino-1-cyclohexyl-3(S)-hydroxy-6-methylheptane (85 mg) was obtained according to a similar manner to that of Example 1-(7) from N-(1,2,3,4-tetrahydroisoquinolin-2-ylcarbonyl)-L-phenylalanine (67 mg) and 2(S)-N$^\alpha$-methyl-N$^{im}$-tosyl-L-histidyl)amino-1-cyclohexyl-3(S)-hydroxy-6-methylheptane (100 mg).

mp: 104°–108° C.

Rf: 0.67 (chloroform: methanol: acetic acid, 8:1:1, V/V).

EXAMPLE 5

(1) To a solution of L-phenylalanine benzyl ester p-toluenesulfonic acid salt (1.71 g) and triethylamine (405 mg) in dry tetrahydrofuran (30 ml), which was cooled to 0° C., was added 4-trifluoromethylphenyl isocyanate (748 mg). The mixture was stirred at the same temperature for 30 minutes. After evaporation of the solvent, the residue was washed with 5% hydrochloric acid, saturated sodium bicarbonate solution and water successively, dried over magnesium sulfate and concentrated under reduced pressure to give N-(4-trifluoromethylphenylcarbamoyl)-L-phenylalanine benzyl ester (1.62 g) as white crystals.

mp: 155°–157° C.

Rf: 0.81 (n-hexane: ethyl acetate, 1:1 V/V).

(2) N-(4-Trifluoromethylphenylcarbamoyl)-L-phenylalanine (1.18 g) was obtained according to a similar manner to that of Example 1-(6) from N-(4-trifluoromethylphenylcarbamolyl)-L-phenylalanine benzyl ester (1.58 g).

mp: 189°–191° C.

Rf: 0.70 (chloroform: methanol: acetic acid, 8:1:1, V/V).

(3) 2(S)-[N-(4-Trifluoromethylphenylcarbamoyl)-L-phenylalanyl-N$^\alpha$-methyl-L-histidyl]amino-1-cyclohexyl-3(S)-hydroxy-6-methylheptane (107 mg) was obtained according to a similar manner to that of Example 1-(7) from N-(4-trifluoromethylphenylcarbamoyl)-L-phenylalanine (73 mg) and 2(S)-(N$^\alpha$-methyl-N$^{im}$-tosyl-L-histidyl)amino-1-cyclohexyl-3(S)-hydroxy-6-methylheptane (100 mg).

mp: 128°–132° C.

Rf: 0.46 (chloroform: methanol, 9:1,V/V) 0.56 (chloroform: methanol: acetic acid 8:1:1,V/V).

EXAMPLE 6

(1) N-(4-Fluorophenylcarbamoyl)-L-phenylalanine benzyl ester (1.54 g) was obtained according to a similar manner to that of Example 5-(1) from L-phenylalanine benzyl ester p-toluenesulfonic acid salt (1.71 g) and 4-fluorophenyl isocyanate (548 mg).

mp: 140°–140.5° C.

Rf: 0.25 (n-hexane: ethyl acetate, 2:1, V/V).

(2) N-(4-Fluorophenylcarbamoyl)-L-phenylalanine (1.11 g) was obtained according to a similar manner to that of Example 1-(6) from N-(4-fluorophenylcarbamoyl)-L-phenylalanine benzyl ester (1.44 g).

mp: 155°–156° C.

Rf: 0.38 (ethyl acetate: benzene: acetic acid, 20:20:1, V/V).

(3) 2(S)-[N-(4-Fluorophenylcarbamoyl)-L-phenylalanyl-N$^\alpha$-methyl-L-histidyl]amino-1-cyclohexyl-3(S)-hydroxy-6-methylheptane (102.6 mg) was obtained according to a similar manner to that of Example 1-(7) from N-(4-fluorophenylcarbamoyl)-L-phenylalanine (68.1 mg) and 2(S)-(N$^{\alpha\text{-}methyl\text{-}Nim}$-tosyl-L-histidyl)amino-1-cyclohexyl-3(S)-hydroxy-6-methylheptane (100.0 mg).

mp: 116°–118° C.

Rf: 0.25 (10% methanol in chloroform).

EXAMPLE 7

(1) N-(n-Butylcarbamoyl)-L-phenylalanine benzyl ester (1.40 g) was obtained according to a similar manner to that of Example 5-(1) from n-butyl isocyanate (397 mg) and L-phenylalanine benzyl ester p-toluenesulfonic acid salt (1.71 g).

mp: 95°–96° C.

Rf: 0.66 (n-hexane: ethyl acetate, 1:1 V/V).

(2) N-(n-Butylcarbamoyl)-L-phenylalanine (977 mg) was obtained according to a similar manner to that of Example 1-(6) from N-(n-butylcarbamoyl)-L-phenylalanine benzyl ester (1.31 g).

Rf: 0.29 (ethyl acetate: benzene: acetic acid, 20:20:1,V/V).

(3) 2(S)-[N-(n-Butylcarbamoyl)-L-phenylalanyl-N$^\alpha$-methyl-L-histidyl]amino-1-cyclohexyl-3(S)-hydroxy-6-methylheptane (64.5 mg) was obtained according to a similar manner to that of Example 1-(7) from N-(n-butylcarbamoyl)-L-phenylalanine (45.1 mg) and 2(S)-

(N$^\alpha$-methyl-N$^{im}$-tosyl-L-histidyl)amino-1-cyclohexyl-3(S)-hydroxy-6-methylheptane (75.8 mg).
mp: 88°-92° C.
Rf 0.30 (10% methanol in chloroform).

EXAMPLE 8

(1) N-(4-Methylpiperazin-1-ylcarbonyl)-L-phenylalanine benzyl ester (762 mg) was obtained according to a similar manner to that of Example 1-(5) from 1-methylpiperazine (441 mg) and L-phenylalanine benzyl ester p-toluene-sulfonic acid salt (1.71 g).
Rf: 0.49 (chloroform methanol acetic acid, 8:1:1,V/V).

(2) N-(4-Methylpiperazin-1-ylcarbonyl)-L-phenylalanine (531 mg) was obtained according to a similar manner to that of Example 1-(6) from N-(4-methylpiperazin-1-yl-carbonyl)-L-phenylalanine benzyl ester (740 mg)
Rf: 0.09 (chloroform: methanol: acetic acid, 8:1:1,V/V).

(3) 2(S)-[N-(4-Methylpiperazin-1-ylcarbonyl)-L-phenylalanyl-N$^\alpha$-methyl-L-histidyl]amino-1-cyclohexyl-3(S)-hydroxy-6-methylheptane (64 mg) was obtained according to a similar manner to that of Example 1-(7) from N-(4-methylpiperazin-1-ylcarbonyl)-L-phenylalanine (52.4 mg) and 2(S)-(N$^\alpha$-methyl-N$^{im}$-tosyl-L-histidyl)amino-1-cyclohexyl-3(S)-hydroxy-6-methylheptane (80 mg)
mp: 100°-108° C.
Rf: 0.10 (chloroform: methanol: acetic acid, 8:2:1,V/V).

EXAMPLE 9

(1) N-(2(S)-Methoxycarbonylpyrrolidin-1-ylcarbonyl)-L-phenylalanine benzyl ester (680 mg) was obtained according to a similar manner to that of Example 1-(5) from L-proline methyl ester hydrochloride (729 mg) and L-phenylalanine benzyl ester p-toluenesulfonic acid salt (1.71 g).
mp: 83°-87° C.
Rf: 0.44 (n-hexane-ethyl acetate, 1:1,V/V).

(2) N-(2(S)-Methoxycarbonylpyrrolidin-1-ylcarbonyl)-L-phenylalanine (470 mg) was obtained according to a similar manner to that of Example 1-(6) from N-(2(S)-methoxycarbonylpyrrolidin-1-ylcarbonyl)-L-phenylalanine benzyl ester (660 mg).
Rf: 0.16 (ethyl acetate benzene: acetic acid, 20:20:1, V/V).

(3) 2(S)-[N-(2(S)-Methoxycarbonylpyrrolidin-1-ylcarbonyl-L-phenylalanyl-N$^\alpha$-methyl-L-histidyl]amino-1-cyclohexyl-3(S)-hydroxy-6-methylheptane (78 mg) was obtained according to a similar manner to that of Example 1-(7) from N-[2(S)-methoxycarbonylpyrrolidin-1-ylcarbonyl]-L-phenylalanine (58 mg) and 2(S)-(N$^\alpha$-methyl-N$^{im}$-tosyl-L-histidyl)amino-1-cyclohexyl-3(S)-hydroxy-6-methylheptane (80 mg).
mp: 92°-98° C.
Rf: 0.42 (chloroform: methanol, 10:1, V/V).

EXAMPLE 10

(1) N-t-Butylcarbamoyl-L-phenylalanine benzyl ester (1.42 g) was obtained according to a similar manner to that of Example 5-(1) from L-phenylalanine benzyl ester p-toluenesulfonic acid salt (1.71 g) and t-butyl isocyanate (397 mg).
Rf: 0.54 (n-hexane: ethyl acetate, 2:1, V/V).

(2) N-t-Butylcarbamoyl-L-phenylalanine (963.4 mg) was obtained according to a similar manner to that of Example 1-(6) from N-t-butylcarbamoyl-L-phenylalanine benzyl ester (1.30 g).
mp: 139°-140° C.
Rf 0.36 (ethyl acetate: benzene acetic acid, 20:20:1, V/V).

(3) 2(S)-(N-t-Butylcarbamoyl-L-phenylalanyl-N$^\alpha$-methyl-L-histidyl)amino-1-cyclohexyl-3(S)-hydroxy-6-methylheptane (61.7 mg) was obtained according to a similar manner to that of Example 1-(7) from N-t-butylcarbamoyl-L-phenylalanine (43.7 mg) and 2(S)-(N$^\alpha$-methyl-N$^{im}$-tosyl-L-histidyl)amino-1-cyclohexyl-3(S)-hydroxy-6-methylheptane (70.8 mg).
mp 115°-123° C.
Rf: 0.26 (methanol: chloroform, 1:9, V/V).

EXAMPLE 11

(1) N-Cyclohexylcarbamoyl-L-phenylalanine benzyl ester (1.52 g) was obtained according to a similar manner to that of Example 5-(1) from cyclohexyl isocyanate (500 mg) and L-phenylalanine benzyl ester p-toluenesulfonic acid salt (1.71 g).
mp: 158°-159° C.
Rf: 0.40 (n-hexane: ethyl acetate, 2:1, V/V).

(2) N-Cyclohexylcarbamoyl-L-phenylalanine (984.6 mg) was obtained according to a similar manner to that of Example 1-(6) from N-cyclohexylcarbamoyl-L-phenylalanine benzyl ester (1.40 g).
Rf: 0.35 (ethyl acetate: benzene: acetic acid, 20:20:1, V/V).

(3) 2(S)-(N-Cyclohexylcarbamoyl-L-phenylalanyl-N$^\alpha$-methyl-L-histidyl)amino-1-cyclohexyl-3(S)-hydroxy-6-methylheptane (63.2 mg) was obtained according to a similar manner to that of Example 1-(7) from N-cyclohexylcarbamoyl-L-phenylalanine (48.0 mg) and 2(S)-(N$^\alpha$-methyl-N$^{im}$-tosyl-L-histidyl)amino-1-cyclohexyl-3(S)-hydroxy-6-methylheptane (71.7 mg).
mp: 115°-123° C.
Rf: 0.29 (methanol: chloroform, 1:9, V/V).

EXAMPLE 12

(1) N-Diethylcarbamoyl-L-phenylalanine benzyl ester (627.6 mg) was obtained according to a similar manner to that of Example 1-(5) from L-phenylalanine benzyl ester p-toluenesulfonic acid salt (1.71 g) and diethylamine (0.46 ml).
Rf: 0.28 (n-hexane: ethyl acetate, 2:1, V/V).

(2) N-Diethylcarbamoyl-L-phenylalanine (447.3 mg) was obtained according to a similar manner to that of Example 1-(6) from N-diethylcarbamoyl-L-phenylalanine benzyl ester (627.6 mg).
Rf: 0.25 (ethyl acetate: benzene: acetic acid, 20:20:1, V/V).

(3) 2(S)-(N-Diethylcarbamoyl-L-phenylalanyl-N$^\alpha$-methyl-L-histidyl)amino-1-cyclohexyl-3(S)-hydroxy-6-methylheptane (53.0 mg) was obtained according to a similar manner to that of Example 1-(7) from N-diethylcarbamoyl-L-phenylalanine (41.2 mg) and 2(S)-(N$^\alpha$-methyl-N$^{im}$-tosyl-L-histidyl)amino-1-cyclohexyl-3(S)-hydroxy-6-methylheptane (77.6 mg).
mp 84°-92° C.
Rf: 0.39 (methanol: chloroform, 1:9, V/V).

EXAMPLE 13

(1) N-Diisopropylcarbamoyl-L-phenylalanine benzyl ester (419.3 mg) was obtained according to a similar manner to that of Example 1-(5) from L-phenylalanine benzyl ester p-toluenesulfonic acid salt (1.71 g) and diisopropylamine (0.57 ml).

Rf: 0.30 (n-hexane: ethyl acetate, 3:1, V/V).

(2) N-Diisopropylcarbamoyl-L-phenylalanine (320.5 m g) was obtained according to a similar manner to that of Example 1-(6) from N-diisopropylcarbamoyl-L-phenylalanine benzyl ester (419 3 mg).

Rf: 0.35 (ethyl acetate benzene: acetic acid, 20:20 1, V/V).

(3) 2(S)-(N-Diisopropylcarbamoyl-L-phenylalanyl-N$^\alpha$-methyl-L-histidyl)amino-1-cyclohexyl-3(S)-hydroxy-6-methylheptane (62.7 mg) was obtained according to a similar manner to that of Example 1-(7) from N-diisopropyl-L-phenylalanine (46.3 mg) and 2(S)-(N$^\alpha$-methyl-N$^{im}$-tosyl-L-histidyl)amino-1-cyclohexyl-3(S)-hydroxy-6-methylheptane (77.3 mg).

mp: 82°–90° C.

Rf: 0.4(methanol: chloroform, 1:9, V/V).

EXAMPLE 14

To a solution of 2(S)-(N-morpholinocarbonyl-L-phenylalanyl-N$^\alpha$-methyl-L-histidyl)amino-1-cyclohexyl-3(S)-hydroxy-6-methylheptane (1.00 g) in ethanol (10 ml) which was cooled to 0° C., was added 4N hydrogenchloride in dioxane (0.47 ml). After the mixture was stirred at the same temperature for 10 minutes, the solvent was evaporated under reduced pressure. This residue was crystallized from ethanol (1 ml) and ethyl acetate (30 ml) to give 2(S)-(N-morpholinocarbonyl-L-phenylalanyl-N$^\alpha$-methyl-L-histidyl)amino-1-cyclohexyl-3(S)-hydroxy-6-methylheptane monohydrochloride (860 mg).

mp: 149°–152° C.

What we claim is:

1. A compound of the formula:

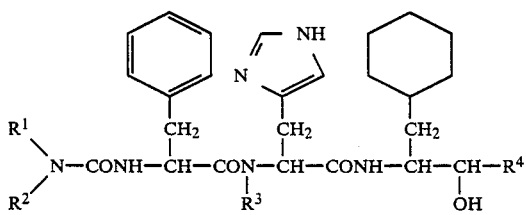

wherein R$^1$ is aryl; aryl substituted with a substituent selected from the group consisting of halogen and halo lower alkyl; lower alkyl or cyclo lower alkyl; and R$^2$ is hydrogen or lower alkyl, or R$^1$ and R$^2$ taken together with the attached nitrogen atom form a heterocyclic group selected from the group consisting of morpholino, thiomorpholino, pyrrolidin-1-yl, piperidino, piperazin-1-yl, pyrrolin-1-yl, 1,4-dihydropyridin-1-yl, 1,2,3,6-tetrahydropyridin-1-yl, 1,2,3,4-tetrahydroisoquinolin-2-yl and 1,2,3,4-tetrahydroquinolin-1-yl, or the above groups substituted with a substituent selected from the group consisting of lower alkyl and lower alkoxycarbonyl; R$^3$ is hydrogen or lower alkyl, and R$^4$ is lower alkyl, or a pharmaceutically acceptable salt thereof.

2. The compound of claim 1, wherein R$^1$ and R$^2$ taken together with the attached nitrogen atom form a heterocyclic group selected from the group consisting of morpholino, thiomorpholino, pyrrolidin-1-yl, piperidino, piperazin-1-yl, pyrrolin-1-yl, 1,4-dihydropyridin-1-yl, 1,2,3,6-tetrahydropyridin-1-yl, 1,2,3,4-tetrahydroisoquinolin-2-yl and 1,2,3,4-tetrahydroquinolin-1-yl, or the above groups substituted with a substituent selected from the group consisting of lower alkyl and lower alkoxycarbonyl.

3. The compound of claim 1, wherein R$^1$ and R$^2$ taken together with the attached nitrogen atom form morpholino, thiomorpholino, pyrrolidin-1-yl, piperazin-1-yl, 1,2,3,4-tetrahydroisoquinolin-2-yl, or the above groups substituted with a substituent selected from the group consisting of lower alkyl and lower alkoxycarbonyl.

4. The compound of claim 3, which is 2(S)-(N-morpholino-carbonyl-L-phenylalanyl-N$^\alpha$-methyl-L-histidyl (amino-1-cyclohexy-3 (S)-hydroxy-6-methylheptane or the hydrochloride thereof.

5. A process for preparing a compound of the formula:

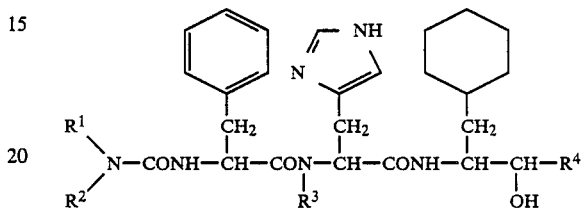

wherein R$^1$ is aryl; aryl substituted with a substituent selected from the group consisting of halogen and halo lower alkyl; lower alkyl or cyclo lower alkyl; and R$^2$ is hydrogen or lower alkyl, or R$^1$ and R$^2$ taken together with the attached nitrogen atom form a heterocyclic group selected from the group consisting of morpholino, thiomorpholino, pyrrolidin-1-yl, piperidino, piperazin-1-yl, pyrrolin-1-yl, 1,4-dihydropyridin-1-yl, 1,2,3,6-tetrahydropyridin-1-yl, 1,2,3,4-tetrahydroisoquinolin-2-yl and 1,2,3,4-tetrahydroquinolin-1-yl, or the above groups substituted with a substituent selected from the group consisting of lower alkyl and lower alkoxycarbonyl; R$^3$ is hydrogen or lower alkyl, and R$^4$ is lower alkyl, or a salt thereof, which process comprises reacting a compound of the formula:

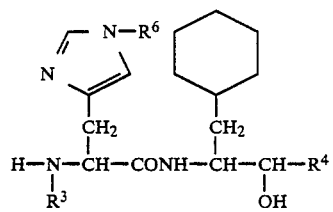

wherein R$^6$ is hydrogen or an N-protective group, and R$^3$ and R$^4$ are each as defined above, or a reactive derivative at the amino group or a salt thereof with a compound of the formula:

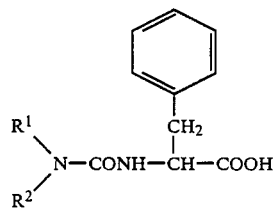

wherein R$^1$ and R$^2$ are each as defined above, or a reactive derivative of the carboxy group or a salt thereof, wherein the reaction is effected in the presence of a solvent which does not substantially adversely influence the reaction.

6. A pharmaceutical composition, comprising an effective amount of a compound of claim 1, in association with a pharmaceutically acceptable carrier or excipient.

7. A method for the therapeutic treatment of hypertension, which comprises administering an effective amount of a compound of claim 1 or a salt thereof to a subject in need of such treatment.

8. The subject of claim 5, wherein said reactive derivative at the carboxy group is an acid halide, acid anhydride, activated amide or activated ester.

9. The process of claim 5, wherein said reactive derivative at the amino group is a Schiff's base imino or enamine group, a silyl derivative or a derivative formed by reaction with phosphorus trichloride or phosgene.

10. The process of claim 5, wherein said reaction is effected in the presence of an alkali metal bicarbonate, tri(lower) alkylamine, pyridine, N-(lower)alkylmorpholine or N,N-di(lower)alkylbenzylamine.

* * * * *